United States Patent

Hammond et al.

[11] Patent Number: 6,047,589
[45] Date of Patent: Apr. 11, 2000

[54] APPARATUS FOR MEASURING A GAS VALUE

[75] Inventors: Paul Stephen Hammond, Ashby de la Zouch; Geoffrey John Parkinson, West Bridgeford; Robert Richard Thurston, Melbourne, all of United Kingdom

[73] Assignee: BG plc, Reading, United Kingdom

[21] Appl. No.: 09/147,165

[22] PCT Filed: Apr. 21, 1997

[86] PCT No.: PCT/GB97/01095

§ 371 Date: Dec. 10, 1998

§ 102(e) Date: Dec. 10, 1998

[87] PCT Pub. No.: WO97/40375

PCT Pub. Date: Oct. 30, 1997

[30] Foreign Application Priority Data

Apr. 22, 1996 [GB] United Kingdom ............ 9608265

[51] Int. Cl.[7] ............................................. G01I 9/00
[52] U.S. Cl. ................................... 73/24.01; 73/23.31
[58] Field of Search ........................... 73/23.31, 24.01, 73/24.06, 31.05

[56] References Cited

U.S. PATENT DOCUMENTS

| 5,285,675 | 2/1994 | Colgate et al. ............... 73/23.2 |
| 5,501,098 | 3/1996 | Cadet et al. ................. 73/24.01 |
| 5,537,854 | 7/1996 | Phillips et al. ............... 73/24.01 |
| 5,635,626 | 6/1997 | Hammond et al. . |
| 5,697,346 | 12/1997 | Beck .......................... 73/23.31 |

FOREIGN PATENT DOCUMENTS 0 117 150  8/1984  European Pat. Off. .

*Primary Examiner*—Hezron Williams
*Assistant Examiner*—Michael Cygan
*Attorney, Agent, or Firm*—Oblon, Spivak, McClelland, Maier & Neustadt, P.C.

[57] ABSTRACT

An energy meter for measuring parameters of fuel gas. The meter has a gas inlet and outlet and a central tube along which the gas flows from inlet to outlet. Ultra-sound transducers and a control form a system whereby the speed of ultra-sound signals traveling through the gas between the transducers is measured and used in the control to calculate the volume of gas which is passed through the meter. The ultra-sound signals pass through apertures in the walls of chambers containing the transducers. Another ultra-sound transducer in the chamber which is connected to the control acts as an emitter and receiver of ultra-sound signals reflected by reflectors. These signals travel through the fuel gas in the chamber and their attenuation is observed and measured by the control when they are received by the transducer. The measured attenuation is used to derive the calorific value and/or Wobbe index of the gas. The control uses the volume of gas and the calorific value and/or Wobbe index to derive the amount of energy in the gas.

18 Claims, 1 Drawing Sheet

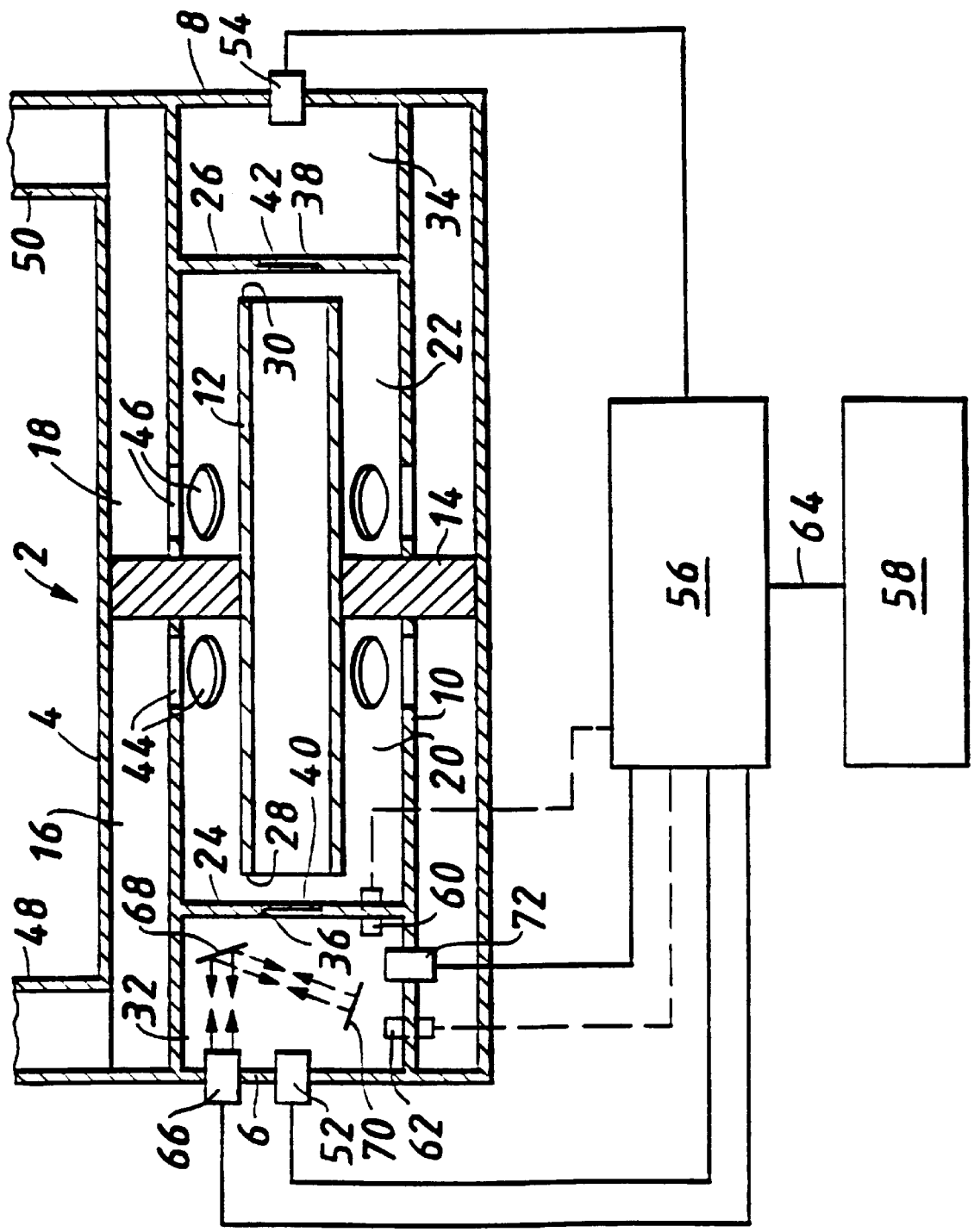

APPARATUS FOR MEASURING A GAS VALUE

BACKGROUND OF THE INVENTION

1. Field of the Invention

This invention relates to apparatus for measuring a gas value, and in particular co apparatus for measuring the calorific value and/or the Wobbe index of combustible fuel gas, and it also relates to apparatus for measuring the amount of energy provided when in the form of combustible fuel gas.

SUMMARY OF THE INVENTION

According to the invention an apparatus for measuring the calorific value and/or the Wobbe index of combustible fuel gas comprises ultra-sound emitter and receiver means for emitting an ultra-sound signal to follow a path through said gas and receive said signal after following said path, means to make a measure of attenuation of the signal between its emission and reception, and means to derive the calorific value and/or Wobbe index from said measured attenuation.

A meter to measure the supply of energy provided by supply of combustible gas may comprise said apparatus formed according to the invention and further comprise means to measure the volumetric amount of gas supplied, and means to derive a value of the amount of energy supplied using said volumetric amount and said calorific value and/or the Wobbe index.

BRIEF DESCRIPTION OF THE DRAWING

The invention will now be further described, by way of example, with reference to the accompanying drawing which shows diagramatically, in cross-section, a gas meter to make volumetric measurement of combustible fuel gas passing therethrough and comprising apparatus formed according to the invention.

DESCRIPTION OF THE PREFERRED EMBODIMENTS

With reference to the drawing, a meter 2 which may be considered as a volumetric gas meter or as an energy meter comprises an outer casing 4 with end walls 6, 8, an inner casing 10 surrounded by the outer casing, and a central open-ended tube 12 surrounded by the inner casing. An impermeable partition 14 surrounds the middle of the central tube 12 and is mounted in a gas tight manner thereon and is in gas tight relation with the inner casing 10 and the outer casing 4. The outer casing 4 defines a space surrounding the inner casing 10, this space being divided by the partition 14 into two separate chambers 16 and 18 surrounding the inner casing. The inner casing 10 defines a space surrounding the central tube 12, this space being divided by the partition 14 into two separate chambers 20 and 22 each bounded by a respective wall 24 or 26 facing a respective end 28 or 30 of the tube 12 and bounding, in combination with the respective end wall 6 or 8 and the inner casing 10, a respective chamber 32 or 34. The wails 24 and 26 of the chambers 32 and 34 each have at least one respective through aperture or window 36 and 38 each facing into the respective open end 28 and 30 of the central tube 12. If desired, the apertures 36 and 38 may each be covered by respective, ultra-sound transparent, gas permeable gauze or membranes 40 and 42, and both chambers 32 and 34 may be lined with acoustic material to avoid unwanted reflections at ultrasonic frequencies. The chamber 16 opens into chamber 20 through a plurality of openings 44, and chamber 22 opens into chamber 18 through a plurality of openings 46. A tube 48 provides an inlet for combustible fuel gas and a tube 50 provides an outlet for the gas. The gas introduced through the inlet 48 follows a labyrinthine path to the inlet end 28 of the central tube 12, the gas then flows along that tube to outlet end 30 and follows a labyrinthine path to the outlet 50. By virtue of the apertures 36 and 38 the gas also fills the chambers 32 and 34. Ultra-sound transducers 52 and 54 under control of control means 56, which includes calculating means comprising computer means, emit and receive ultra-sound signals, via apertures 36 and 38, passing along the interior of the central tube 12.

The signals between the transducers 52 and 54 are used in known manner to calculate in control means 56, the speed of sound in the gas, the speed of sound being used in known manner to calculate the amount of gas passing through the meter 2 in unit time, i.e., the volumetric flow rate. The control means 56 may integrate the flow rate with respect to time, in known manner, to enable recorder means 58 to produce a record or indication of the total volume of gas which has passed through the meter 2 over a period of time. If the temperature of the gas is variable, temperature sensing means 60 exposed to gas in the meter 2 may be provided to give a signal indicative of gas temperature for use in known manner by the control means 56 in making the speed of sound and volumetric flow rate calculations. Also if the gas is supplied to the meter 2 at variable pressure a pressure sensor 62 may be provided to give a signal indicative of gas pressure for use by the control means 56 in making the speed of sound and volumetric flow rate calculations.

The temperature sensor 60 and/or the pressure sensor 62 may be in either of the labyrinthine gas flow paths in the meter or in a relatively still gas region, for example as in the drawing in the chamber 32, where there is little or no movement of the gas.

The control means 56 may be arranged to observe attenuation of ultra-sound signals resultant from their passage between the transducers 52 and 54. The ultra-sound signals of which attenuation is observed may be the same as those used for measuring the velocity of the ultra-sound in the gas when the meter 2 is measuring the volumetric flow-rate or they may be different signals in the sense of being emitted at different times. In the latter case the ultra-sound signals may be emitted at a different frequency or frequencies when used in the attenuation measurement from the frequency used in the speed of ultra-sound measurement.

Stored in the control means 56 are different sets of predetermined reference data for a given fuel gas, each set of data comprising an attenuation of ultra-sound in gas value and a speed of ultra-sound in gas value which may all be corrected to standard temperature and pressure, and each set correlated to a particular calorific value and/or Wobbe index. The measured values of ultra-sound signal attenuation and the speed of ultra-sound may be corrected in the control means 56 to standard temperature and/or pressure using the value(s) of temperature and/or pressure observed by the temperature sensor 60 and/or the pressure sensor 62 and are fitted against the reference sets until a reference set is discovered having values corresponding most closely to the measured values. The inference is drawn by the control means 56 that the calorific value and/or Wobbe index correlated to that reference set are/is the calorific value and/or Wobbe index of the fuel gas passing through the meter 2, and the control means 56 may send a signal on path 64 conveying the inferred calorific value and/or Wobbe index to the recorder means 58 where a record of the calorific value and/or Wobbe index may be produced in some suitable form.

As an alternative or in addition to using the transducers 52 and 54 in the measurement of ultra-sound signal attenuation and/or the speed of ultra-sound for the purposes of measuring the calorific value and/or Wobbe index of the fuel gas another ultra-sound transducer 66 is disposed in the chamber 32 in conjunction with ultra-sound reflectors 68 and 70. Ultra-sound signals emitted by the transducer 66 under control by the control means 56 are received by it after reflection back from the reflector 70. The difference in signal strength between that emitted by the transducer and that received back by it is an indication of signal attenuation which is observed by the control means 56 and may be corrected to standard temperature and/or pressure and compared with the reference data for use in drawing the inference of what the calorific value and/or Wobbe index is. Ultra-sound signals of different frequencies, determined by the control means 56, may be emitted by the transducer and the attenuation of each observed and used in calorific value and/or Wobbe index determination.

The system 56, 66, 68, 70 may also be used for measuring the speed of ultra-sound in the gas and this measurement corrected for standard temperature and/or pressure and used for the drawing of the inference of the calorific value and/or Wobbe index. The frequency of the ultra-sound signal used in the speed of ultra-sound measurement may differ from that or those used in signal attenuation measurement.

The aforesaid reference data correlated to the calorific value and/or Wobbe index may include in each set data comprising a thermal conductivity value and/or a gas specific heat value. The value of the thermal conductivity of the gas and/or the specific heat capacity of the gas is measured (in known manner) by the control means 56 in response to signals from a thermal conductivity sensor 72 (known per se) for example a TCS20 thermal conductivity sensor sold by Hartmann & Braun. The sensor 72 is preferably mounted in a still gas region (as indicated in the drawing). The observed values of the gas thermal conductivity value and/or a gas specific heat capacity is/are corrected to standard temperature and/or pressure and can be used for comparison with aforesaid reference data sets in the process by which the calorific value and/or the Wobbe index of the gas is inferred.

The meter 2 can be used as an energy meter. The control means 56 can use the volumetric flow rate and the value of the calorific value and/or Wobbe index in a calculation or process to derive the amount of energy supplied by provision of the fuel gas; the energy becoming sensible heat when the gas is burned. The energy supplied may be recorded in suitable form by the recorder means 58. The recorder means 58 may be some distance from the meter 2 and the control means 56 may be arranged to make a calculation to derive a monetary value of the energy supplied, which monetary value may be recorded in suitable form by said recorder means.

We claim:

1. An apparatus for measuring at least one of a calorific value and a Wobbe index of a combustible fuel gas comprising:

means for emitting an ultra-sound signal to follow a path through said gas;

means for receiving said signal after following said path;

means for measuring an attenuation of the signal between emission and reception; and means for deriving at least one of a calorific value and Wobbe index from said measured attenuations.

2. Apparatus as claimed in claim 1, further comprising:

means for measuring a speed of said ultra-sound signal in said gas, wherein the means for deriving uses the measured speed in deriving said at least one of a calorific value and Wobbe index.

3. Apparatus as claimed in claim 2, further comprising:

means for sensing at least one of a thermal conductivity and a specific heat capacity of the gas, wherein the means for deriving uses at least one of the thermal conductivity and specific heat capacity in deriving said at least one of a calorific value and Wobbe index.

4. Apparatus as claimed in claim 3, wherein said means for deriving comprises:

means for comparing said measured attenuation and at least one of said speed, thermal conductivity, and specific heat capacity with a plurality of prederived values of attenuation, speed, thermal conductivity and specific heat, wherein each of said prederived values is correlated to a particular calorific value and to a particular Wobbe index, whereby from said comparison said at least one of a calorific value and Wobbe index is inferred.

5. Apparatus as claimed in claim 3, in which the sensing means comprises a sensor exposed to the gas in a still gas region where there is little or no gas movement.

6. Apparatus as claimed in claim 1, further comprising:

means for measuring a speed of said ultra-sound signal in said gas;

temperature sensing means for sensing a temperature of the gas, wherein said sensed temperature is used to correct at least one of said measured attenuation and the measured speed of said ultra-sound signal.

7. Apparatus as claimed in claim 3 further comprising:

temperature sensing means and pressure sensing means for sensing a temperature and a pressure of the gas, wherein sensed temperature and pressure values are used to correct at least one of said measured attenuation, and said at least one of said measured thermal conductivity and said measured specific heat capacity to standard temperature and pressure.

8. Apparatus as claimed in claim 1, wherein said means for emitting emits ultra-sound signals at different frequencies, and said means for measuring an attenuation of the signal between emission and reception further measures attenuation of the ultra-sound signals emitted at different frequencies.

9. Apparatus as claimed in claim 2, wherein said ultra-sound signal measured by said means for measuring attenuation is a first frequency, and said ultra-sound signal measured by said means for measuring speed is a second frequency different from said first frequency.

10. Apparatus as claimed in claim 4, in which the sensing means comprises a sensor exposed to the gas in a still gas region where there is little or no gas movement.

11. Apparatus as claimed in claim 2, further comprising:

temperature sensing means for sensing a temperature of the gas, wherein said sensed temperature is used to correct at least one of said measured attenuation and speed.

12. Apparatus as claimed in claim 4, further comprising:

temperature sensing means and pressure sensing means for sensing a temperature and a pressure of the gas, wherein said sensed temperature and pressure is used to correct at least one of said measured attenuation, and said at least one of said measured thermal conductivity and said measured specific heat capacity to standard temperature and pressure.

13. Apparatus as claimed in claim 2, wherein said means for measuring an attenuation of the signal between emission and reception further measures attenuation of ultra-sound signals emitted at different frequencies.

14. Apparatus as claimed in claim 3, wherein said means for measuring an attenuation of the signal between emission and reception further measures attenuation of at least two ultra-sound signals emitted at different frequencies.

15. A gas meter through which a combustible gas passes, comprising:

a first means for emitting a first ultra-sound signal to follow a first path through said gas;

a first means for receiving said first ultra-sound signal after following said first path;

first means for measuring an attenuation of the first ultra-sound signal between emission and reception;

means for deriving at least one of a calorific value and Wobbe index from said attenuation measured by said first means for measuring;

a second means for emitting a second ultra-sound signal to follow a second path through said gas;

a second means for receiving said second ultra-sound signal after following said second path;

second means for measuring a speed of said second ultra-sound signal between emission and reception; and means for deriving a volumetric flow rate and a volumetric amount of the gas passed through the meter from said speed measured by said second means for measuring speed.

16. A meter as claimed in claim 15, further comprising:

means for deriving an amount of energy supplied by the gas passed through said meter, wherein said amount of energy is derived from said volumetric amount of gas passed through said meter and said at least one of a calorific value and Wobbe index.

17. Apparatus as claimed in claim 1, wherein said means for emitting an ultra-sound signal and said means for receiving the ultra-sound signal comprises a transducer adapted to emit and receive the ultrasound signal.

18. Apparatus as claimed in claim 1, wherein said means for emitting an ultra-sound signal comprises a first transducer adapted to emit the ultrasound signal, and said means for receiving the ultra-sound signal comprises a second transducer adapted to receive the ultrasound signal.

* * * * *